US005696246A

United States Patent [19]
Schmidt et al.

[11] Patent Number: 5,696,246
[45] Date of Patent: Dec. 9, 1997

[54] PROCESS FOR THE SPECIFIC SYNTHESIS OF β-GLYCOSIDICALLY LINKED N-ACETYLPYRANOSIDE DERIVATIVES

[75] Inventors: Wolfgang Schmidt, Frankfurt; Gerhard Kretzschmar, Eschborn, both of Germany

[73] Assignee: Hoechst Aktiengesellschaft, Frankfurt, Germany

[21] Appl. No.: 648,717

[22] Filed: May 16, 1996

[30] Foreign Application Priority Data

May 16, 1995 [DE] Germany ................. 195 17 889.0

[51] Int. Cl.$^6$ ........................................... C07H 1/00
[52] U.S. Cl. ............................... 536/18.5; 536/18.6
[58] Field of Search ........................... 536/18.5, 18.6

[56] References Cited

FOREIGN PATENT DOCUMENTS

WO 94/19360  9/1994  WIPO.

OTHER PUBLICATIONS

Stahl et al. "Synthesis of Deoxy Sialyl Lewis Analogues, Potential Selection Antagonists," *Chem. Int. Ed. Engl.*, 33: 2096 (1994).
Higashi et al. "Novel Stereoselective Glycosidation by the Combined Use of Trityl Halide and Lewis Acid," *Chem. Pharma. Bull*, 38(12): 3280–3282 (1990).
Kohli et al. "The Triphenylmethyl (Trityl) Group And Its Uses in Nucleotide Chemistry," *Tetrahedron Lett.*, 21: 2683–2686 (1980).
Amarnath et al. "Chemical Synthesis of Oligonucleotides," *Chemical Rev.*, 77(2): 183, 189, 213 (1977).
Hakamori "Aberrant Glycosylation in Tumors and Tumor-Associated Carbohydrate Antigens," *Adv. Cancer Res.*, 52: 257 (1989).
Bevilacqua et al. "Endothelial Leukocyte Adhesion Molecule 1: An Inducible Receptor for Neutrophils Related to Complement Regulatory Proteins and Lectins," *Science*, 243: 1160 (1989).
Feizi et al. "Carbohydrates as Antigenic Determinants of Glycoproteins," *Biochem J.*, 245: 1 (1987).
Schmidt "Recent Developments in the Synthesis of Glycoconjugates," *Pure & Appl. Chem.*, 61: 1257 (1989).
Mukaiyama et al. "A Facile Synthesis of α–Ribosides From the Corresponding 1–O–ACYL Sugars and Alcohols in the Presence of Trityl Perchlorate," *Chem. Lett.*, pp. 907–910 (1984).
Horton "2-Acetamido-3,46-Tri-O-Acetyl-2-Deoxy-α-D-Glucopyranosyl Chloride," *Org. Synth.*, Coll., vol. V: 1 (1973).
Kallin et al. "Synthesis of p–Trifuloroacetamidophenylethyl ... " *J. Carbohydr. Chem.*, 9: 721 (1990).
Phillips et al. "ELAM–1 Mediates Cell Adhesion by Recognition of a Carbohydrate Ligand, Sialyl–Le$^x$," *Science*, 250: 1130 (1990).
Kumar et al. "Preparation of Ether–Linked ... " *Tetrahedron Lett.*, 35: 505 (1994).

*Primary Examiner*—Elli Peselev
*Attorney, Agent, or Firm*—Foley & Lardner

[57] ABSTRACT

A process for the stereospecific synthesis of β-glycosidically linked N-acetylglucosamine derivatives is provided, wherein a protected α-(N-acetyl-2-amino-2-deoxy)-β-pyranosyl halide is coupled to a glycosyl acceptor using zinc chloride and a 4,4'-dialkoxytriphenylmethyl halide as catalysts.

10 Claims, No Drawings

PROCESS FOR THE SPECIFIC SYNTHESIS OF β-GLYCOSIDICALLY LINKED N-ACETYLPYRANOSIDE DERIVATIVES

FIELD OF THE INVENTION

The invention provides processes for the stereoselective synthesis of β-glycosidically linked N-acetyl-2-amino-2-deoxypyranoside derivatives and in particular of N-acetyl-2-amino-2-deoxy-β-D-glucopyranosides.

BACKGROUND OF THE INVENTION

The important role played by carbohydrates in biologically important recognition processes has been appreciated only recently. For reviews see: Feizi, *Biochem. J.* 245:1 (1987); Hakamori, *Adv. Cancer Res.* 52:257 (1989); Bevilacqua et al., *Science* 243:1160 (1989).

Carbohydrates, with their many asymmetric centers that are capable of conveying large amounts of stereochemical information, can be considered as important biological information carriers, in much the same fashion as proteins and nucleic acids. The arrangement of carbohydrates as ligands on a cell surface enables them, via receptor-ligand interactions, to play a crucial part in intercellular communication and recognition processes. The increased understanding of the important role played by carbohydrates in physiologically relevant recognition processes has, therefore, led to increased interest in methods of carbohydrate synthesis.

An important building block in oligosaccharide synthesis is N-acetylglucosamine (N-acetyl-2-amino-2-deoxy-D-glucopyranose) (1), which occurs in many physiologically important oligosaccharide structures. See, for example, Paulson et al., *Science* 250:1130 (1990).

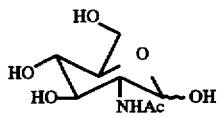

Oligosaccharide synthesis requires covalent coupling of stereochemically complex monosaccharide units, often containing 4 or 5 hydroxyl groups each having only slightly differing chemical reactivity. Stereospecific oligosaccharide synthesis requires, therefore, a sophisticated protecting group strategy that allows selective introduction and removal of a variety of protecting groups.

Synthesis of glycosides requires activation at the C-1 position of the glycosyl donor with simultaneous protection of other hydroxyl groups to prevent their participation in unwanted side reactions, including non-regiospecific coupling reactions. Glycosidic linkages between the glycosidic donor and acceptor can form with either an α- or β-configuration at the anomeric carbon, and stereoselective formation of either the α- or β-anomer is often problematic. Many synthetic schemes have been devised to allow preferential formation of one anomer or the other. For a review, see Schmidt, *Pure & Appl. Chem.* 61:1257 (1989). Many of these processes, however, often lead to only low yields or poor α/β selectivities, and have the further disadvantage of using activating catalysts that are expensive or that use toxic heavy metals.

To prepare N-acetylglucosamine derivatives, a variety of very different N-acetylglucosamine donors has been employed. See, for example, Mukaiyama et al., *Chem. Lett.* 907 (1984); Higashi, *Chem. Pharm. Bull.* 38:3280 (1990). For efficient glycoside synthesis on a large scale, ready availability of the N-acetyl glucosamine donor is of particular importance. Of the various donors that have been used, the peracetylated chloride of N-acetyl-2-amino-2-deoxy-D-glucopyranose, N-acetyl-2-amino-2-deoxy-3,4,6-tri-O-acetyl-α-D-glucopyranosyl chloride (2), can readily be prepared in a single step from N-acetylglucosamine by reaction with acetyl chloride. See Horton, *Org. Synth., Coll. Vol. V,* 1 (1973).

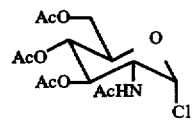

A suitable catalyst for formation of glycosidic linkages has proven to be zinc chloride which allows preparation of α/β ratios of up to 1:5 in the reaction of N-acetyl-2-amino-2-deoxy-3,4,6-tri-O-acetyl-α-D-glucopyranosyl chloride (2) with lactose derivatives. See Norberg, *J. Carbohydr. Chem.* 9:721 (1990).

In another report containing little useful experimental detail, the glycosyl donor (2) was reacted with various glycosyl acceptors using zinc chloride as catalyst in the presence of various cocatalysts. See Bittman, *Tetrahedron Lett.*, 35:505 (1994). The cocatalyst employed was, for example, trityl chloride (triphenylmethyl chloride). This catalyst combination, however, required long reaction times, and caused loss of β-selectivity due to unwanted anomerization effects. In addition, many glycosyl acceptors failed to react with the glycosyl donor (2) under these conditions.

It is apparent, therefore, that a stereoselective method of preparing glycosides of N-acetylglucosamine is greatly to be desired. It is also desirable that such a method should allow short reaction times, use an inexpensive, non-toxic catalyst, and be amenable to use on a large scale.

SUMMARY OF THE INVENTION

It is therefore an object of the present invention to provide a process for the synthesis of β-glycosidically linked N-acetylglucosamine derivatives, in particular of N-acetyl-2-amino-2-deoxy-β-D-glucopyranosides, which proceeds in high yield and with high β-selectivity, which does not cause anomerization of the glycosidic bond produced, and which is applicable to a large number of glycosyl acceptors, in particular alcohols.

In accomplishing these objects, there has been provided a method for preparing an α-(N-acetyl-2-amino-2-deoxy)-β-pyranoside, comprising contacting a mixture of a protected α-(N-acetyl-2-amino-2-deoxy)-α-pyranosyl chloride and a glycosyl acceptor in a solvent with zinc chloride and a 4,4'-dialkoxytriphenylmethyl halide. In a preferred embodiment the 4- and 4'-alkoxy groups of the 4,4'-dialkoxytriphenylmethyl halide are the same or different, and each is selected from the group consisting of methoxy-, ethoxy-, and isopropyloxy-. In a further preferred embodiment, the 4,4'-dialkoxytriphenylmethyl halide is a 4,4'-dimethoxytriphenylmethyl halide, and the halide atom is chloride, bromide, or iodide, and preferably is chloride.

In another preferred embodiment, the zinc chloride and 4,4'-dialkoxytriphenylmethyl halide are employed in a molar ratio of about 1:1, preferably in dichloromethane as solvent. In yet another preferred embodiment, the protected α-(N-acetyl-2-amino-2-deoxy)-β-pyranosyl chloride is an N-acetyl-2-amino-2-deoxy-β-D-glucopyranosyl chloride, where the hydroxyl groups of said N-acetyl-2-amino-2-deoxy-β-D-glucopyranosyl chloride are protected as esters.

More preferably, the esters are acetate esters and the protected α-(N-acetyl-2-amino-2-deoxy)-β-pyranosyl chloride is N-acetyl-2-amino-2-deoxy-3,4,6-tri-O-acetyl-α-D-glucopyranosyl chloride.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The present invention provides a process for preparing α-(N-acetyl-2-amino-2-deoxy)-β-pyranosides by reacting a protected α-(N-acetyl-2-amino-2-deoxy)pyranosyl chloride with a glycosyl acceptor in the presence of zinc chloride and a 4,4'-dialkoxytriphenylmethyl halide as a cocatalyst.

The method is applicable to the coupling of any protected α-(N-acetyl-2-amino-2-deoxy)-β-pyranose in which the non-anomeric hydroxyl groups are protected against unwanted reactions by means of protecting groups that are stable to the conditions of the coupling reaction. Suitable pyranoses include N-acetylglucosamine and derivatives, and N-acetylgalactosamine (N-acetyl-2-amino-2-deoxy-D-galactopyranose). Other suitable pyranoses are well known to the skilled artisan.

Generally, the reaction is carried out by first protecting all of the reactive hydroxyl groups in the pyranose, followed by converting the protected anomeric hydroxyl group to the anomeric halide. This conversion may be carried out by well-known methods. The protection reaction and formation of the anomeric halide also may be carried out simultaneously. For example, N-acetyl-2-amino-2-deoxy-β-D-glucopyranose is simultaneously acetylated and converted to the α-anomeric chloride by treatment with acetyl chloride. See Horton, *supra*. In a preferred embodiment the anomeric chloride is used.

Protecting groups that are stable under the reaction conditions are well known to the skilled artisan. See, for example. Greene, *Protecting Groups in Organic Synthesis*, (Wiley Interscience, 1981). In a preferred embodiment the protecting groups are esters, more preferably acetates. Methods for formation and removal of suitable protecting groups are well known in the art. See Greene, *supra*.

Once a suitably protected anomeric halide is prepared, the coupling reaction is carried using a glycosidic acceptor alcohol. The acceptor alcohol may be a straight or branched chain alkyl alcohol, an aryl alcohol, or an unprotected hydroxyl group of another carbohydrate moiety. Other alcohol-containing compounds suitable for use in the coupling are well known to one skilled in the art of carbohydrate synthesis.

The coupling reaction uses a catalyst of zinc chloride with a cocatalyst of a 4,4'-dialkoxytriphenylmethyl halide. The 4- and 4'-alkoxy groups on the cocatalyst may be the same or different and preferably are selected from the group consisting of methoxy-, ethoxy-, and isopropyloxy-. In a preferred embodiment, the cocatalyst is a 4,4'-dimethoxytriphenylmethyl halide, more preferably 4,4'-dimethoxytriphenylmethyl chloride. It should be noted, however, that the identity of the halide atom in the cocatalyst does not affect the yield or β-stereoselectivity of the process.

Methods of preparing 4,4'-dialkoxytriphenylmethyl halides are well known in the art. For example, the preparation of 4,4'-dimethoxytriphenylmethyl chloride, bromide and iodide is described in Roedig, *Houben Weyl*, Vol. V/4, 1960, 595 ff.

In a preferred embodiment, the zinc chloride and the 4,4'-dialkoxytriphenylmethyl halide are employed in a molar ratio of about 1:1. The present invention is not limited to this ratio, however, and routine methods of optimizing catalyst/cocatalyst ratios without undue experimentation are well known to those skilled in the art of carbohydrate synthesis. For example, the ratio of each component can be independently and systematically varied, starting at about 1:1, and the resulting yield and β-selectivity of the product is then determined for each catalyst/cocatalyst ratio to arrive at the optimal ratio. The solvent for the coupling reaction can be any solvent in which both reactants are at least partially soluble, and that is inert to the reaction conditions of the coupling. In a preferred embodiment, the solvent is dichloromethane.

Use of the catalyst combination as set forth above leads to significantly shorter reaction times than other known coupling methods, even when the reaction is performed on a large scale. In conventional coupling methods a significant excess of the donor (3) is used to ensure high yields of the coupled product. The modified methods of the present invention allow a much lower excess of the donor to be used, increasing the reagent efficiency of the reaction. In addition, there is little restriction on the nature of the donor alcohol coupling component, allowing coupling of a wide variety of very different alcohols.

Other advantages of the present invention over prior art methods include improved ease of chromatographic purification of the glycosidic products. Moreover, the shorter reaction times lead to fewer deleterious anomerization effects, allowing specific synthesis of β-glycosidically linked N-acetylpyranoside derivatives, and particularly N-acetylglucosamine derivatives, in high yields.

The present invention, thus generally described, will be understood more readily by reference to the following examples, which are provided by way of illustration and are not intended to be limiting of the present invention. In the following examples, the reactions of N-acetyl-2-amino-2-deoxy-3,4,6-tri-O-acetyl-α-D-glucopyranosyl chloride (2) with different glycosyl acceptors in each case according to the following reaction scheme are described. The compounds (3a–d) obtained in this process are useful intermediates in the synthesis of complex oligosaccharides. See, for example Stahl et al., *Angew. Chem. Int. Ed. Engl.*, 33:2096 (1994).

EXAMPLES $^1$H-NMR spectra were recorded at 300 MHz using a Bruker WT 300. Ready-to-use silica gel 60 F254 TLC plates from Merck were employed for thin-layer chromatography (TLC). Silica gel 60 (particle size 0.040–0.063 mm, 230–400 mesh) from Merck was used for column chromatography.

Example 1: Preparation of N-benzyloxycarbonyl-6-aminohexyl-N-acetyl-2-amino-2-deoxy-3,4,6-tri-O-acetyl-β-D-gluco-pyranoside (3a)

The chloride (2) (282 g, 0.773 mol, 1.3 eq.) and 6 aminohexanol (150 g, 0.595 mol, 1 eq.) were added to a suspension of zinc(II) chloride (80 g, 0.595 mol, 1 eq.) and 4,4'-dimethoxytrityl chloride (205 g, 0.595 mol, 1 eq.) in dry dichloromethane (3 l). The mixture was stirred at room temperature for 3 h until reaction was complete as shown by thin layer chromatography ("TLC")(methylene chloride/methanol 20:1). Methylene chloride (1 l) was added, and the mixture was washed with saturated aqueous sodium hydrogen carbonate. Solvent was remover in vacuo and the residue was purified by column chromatography (methylene chloride/methanol 100:1–20:1) to yield the glycoside (3a) (321 g, 93%).

$R_f$: 0.35 (methylene chloride/methanol 20:1)

$^1$H-NMR (300 MHz, CDCl$_3$): 7.38–7.28 (m, 5H); 6.00 (d, 1H); 5.29 (dd, 1H); 5.12 (dd, 1H); 5.05 (dd, 1H); 4.90 (t, 1H); 4.63 (d, J=8.0 Hz, 1H); 4.25 (dd, 1H); 4.11 (dd, 1H); 3.90–3.72 (m, 2H); 3.67–3.58 (m, 1H); 3.52–3.43 (m, 1H); 3.26–3.08 (m, 2H); 2.12–1.94 (4 s, 12H); 160–1.43 (m, 4H); 1.39–1.28 (m, 4H) ppm.

Example 2: Preparation of N-phthaloylamido-2-aminoethyl-N-acetyl-2-amino-2-deoxy-3,4,6-tri-O-acetyl-β-D-glucopyranoside (3b)

Chloride (2) (4.97 g, 1.3 eq.) and N-hydroxyethyl-phthalimide (2.00 g, 1 eq.) were added to a suspension of zinc(II) chloride (1.39 g, 1 eq.) and 4,4'-dimethoxytrityl chloride (1.22 g, 1 eq.) in dry dichloromethane (40 ml). The mixture was stirred at room temperature for 1 h until reaction was complete as shown by TLC (methylene chloride/methanol 20:1). Methylene chloride was added, and the mixture was washed with saturated aqueous sodium hydrogen carbonate solution. Solvent was removed in vacuo, and the residue was purified by column chromatography (methylene chloride/methanol 100:1–40:1) to yield the glycoside (3b) (4.94 g, 91%).

$R_f$: 0.35 (methylene chloride/methanol 20:1)

$^1$H-NMR (300 MHz, CDCl$_3$): 7.9 (m, 2H); 7.7 (m, 2H); 5.95 (d, 1H); 5.30–5.05 (m, 2H); 4.95 (d, J=8.0 Hz, 1H); 4.20–3.890 (m, 7H); 3.60 (dd, 1H), 2.10–2.00 (4 s, 12H) ppm.

Example 3: Preparation of pentyl-N-acetyl-2-amino-2-deoxy-3,4,6-tri-O-acetyl-β-D-glucopyranoside (3c)

The chloride (2) (5.38 g, 1.3 eq.) and n-pentanol (2.00 g, 1 eq.) were added to a suspension of zinc(II) chloride (1.55 g, 1 eq.) and 4,4'-dimethoxytrityl chloride (3.84 g, 1 eq.) in dry dichloromethane (40 ml). The mixture was stirred at room temperature for 1 h until reaction was complete as shown by TLC (methylene chloride/methanol 20:1). Methylene chloride was added and the mixture was washed with saturated sodium hydrogen carbonate solution. Solvent was removed in vacuo, and the residue was purified by column chromatography (methylene chloride/methanol 100:1–40:1) to yield the glycoside (3c) (4.01 g, 85%).

$R_f$: 0.35 (methylene chloride/methanol 20: 1)

$^1$H-NMR (300 MHz, CDCl$_3$): 7.38–7.28 (m, 5H); 6.00 (d, 1H); 5.30 (dd, 1H); 5.15 (dd, 1H); 5.05 (dd, 1H); 4.95 (t, 1H); 4.65 (d, J=8.5 Hz, 1H); 4.20 (dd, 1H); 4.10 (dd, 1H); 3.90–3.70 (m, 2H); 3.67–3.58 (m, 1H); 3.52–3.43 (m, 1H); 2.12–1.94 (4 s, 12H); 165–1.30 (m, 8H) ppm.

Example 4: Preparation of N-benzyloxycarbonyl-6-aminohexyl-N-acetyl-2-amino-2-deoxy-3-O-(N-acetyl-2-amino-2-deoxy-3,4,6-tri-O-acetyl-β-D-glucopyranosyl)-4,6-O-benzylidene-β-D-glucopyranoside (3d)

The chloride (2) (1.72 g, 1.3 eq.) and N-benzyloxycarbonyl-6-aminohexyl-N-acetyl-2-amino-2-deoxy-4,6-O-benzylidene-β-D-glucopyranoside (2.00 g, 1 eq.) were added to a suspension of zinc(II) chloride (0.49 g, 1 eq.) and 4,4'-dimethoxytrityl chloride (1.23 g, 1 eq.) in dry dichloromethane (40 ml). The mixture was stirred at room temperature for 1 h until reaction was complete as shown by TLC (methylene chloride/methanol 20:1). Methylene chloride was added and the mixture was washed with saturated sodium hydrogen carbonate solution. Solvent was removed in vacuo, and the residue was purified by column chromatography (methylene chloride/methanol 100:1–40:1) to yield the glycoside (3d) (2.74 g, 86%).

$R_f$: 0.35 (methylene chloride/methanol 20:1)

$^1$H-NMR (300 MHz, CDCl$_3$): 7.50–7.25 (m, 10H); 5.80 (m, 1H); 5.55 (s, 1H); 5.18 (m, 1H); 5.05 (s, 2H); 4.75 (d, 1H); 4.69 (d, J=8.0 Hz, 1H); 4.60 (d, J=8.0 Hz, 1H); 4.32–4.00 (m, 5H); 3.80 (m, 3H); 3.50 (m, 1H); 3.17 (m, 2H); 2.15–1.90 (5 s, 15H); 1.60–1.35 (m, 8H) ppm.

The scheme below shows the reaction scheme and structures for the preparation of compounds (3a–d) as set forth in Examples 1–4.

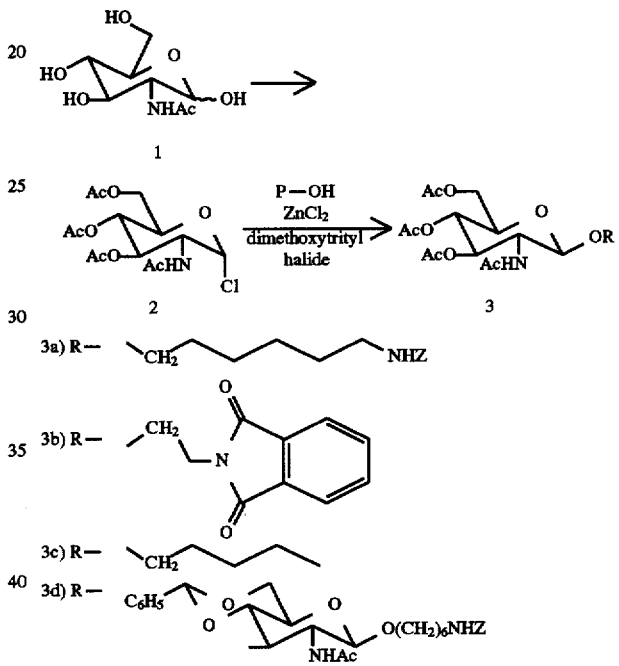

The disclosure of all publications cited above are expressly incorporated herein by reference in their entireties to the same extent as if each were incorporated by reference individually. The disclosure of German Patent Application No. 19517889.0 (filed May 16, 1995), for which benefit under 35 USC § 119 is claimed, is expressly incorporated herein in its entirety.

What is claimed is:

1. A method for preparing an α-(N-acetyl-2-amino-2-deoxy)-β-pyranoside, comprising contacting a mixture of a protected α-(N-acetyl-2-amino-2-deoxy)-α-pyranosyl chloride and a glycosyl acceptor in a solvent with zinc chloride and a 4,4'-dialkoxytriphenylmethyl halide.

2. The method of claim 1, wherein the 4- and 4'-alkoxy groups of said 4,4'-dialkoxytriphenylmethyl halide are the same or different, and each is selected from the group consisting of methoxy-, ethoxy-, and isopropyloxy-.

3. The method of claim 2, wherein said 4,4'-dialkoxytriphenylmethyl halide is a 4,4'-dimethoxytriphenylmethyl halide, and wherein said halide atom is chloride, bromide, or iodide.

4. The method of claim 3, wherein said 4,4'-dimethoxytriphenylmethyl halide 4,4'-dimethoxytriphenylmethyl chloride.

5. The method of claim 1, wherein said zinc chloride and said 4,4'-dialkoxytriphenylmethyl halide are employed in a molar ratio of about 1:1.

6. The method of claim 1, wherein said solvent is dichloromethane.

7. The method of claim 1, wherein the hydroxyl groups of said protected α-(N-acetyl-2-amino-2-deoxy)-β-pyranosyl chloride are protected as esters.

8. The method of claim 7, wherein said esters are acetate esters.

9. The method of claim 7, wherein said protected N-acetyl-2-amino-2-deoxy-β-pyranosyl chloride is a protected N-acetyl-2-amino-2-deoxy-β-D-glucopyranosyl chloride.

10. The method of claim 9, wherein said protected N-acetyl-2-amino-2-deoxy-β-D-glucopyranosyl chloride is N-acetyl-2-amino-2-deoxy-3,4,6-tri-O-acetyl-α-D-glucopyranosyl chloride.

* * * * *